United States Patent [19]
Salter

[11] Patent Number: 5,137,017
[45] Date of Patent: Aug. 11, 1992

[54] DEMAND OXYGEN SYSTEM

[75] Inventor: Peter Salter, Tehachapi, Calif.

[73] Assignee: Salter Labs, Arvin, Calif.

[21] Appl. No.: 669,468

[22] Filed: Mar. 14, 1991

Related U.S. Application Data

[63] Continuation of Ser. No. 337,375, Apr. 13, 1989, abandoned.

[51] Int. Cl.$^5$ .............................................. A61M 15/08
[52] U.S. Cl. ........................... 128/207.18; 128/204.18; 128/204.26
[58] Field of Search ....................... 128/204.18, 203.22, 128/204.26

[56] References Cited

U.S. PATENT DOCUMENTS

| | | | |
|---|---|---|---|
| 3,172,407 | 3/1965 | Pechmann | 128/207.18 |
| 4,054,133 | 10/1977 | Myers | 128/207.18 |
| 4,989,599 | 2/1991 | Carter | 128/207.18 |

Primary Examiner—Edgar S. Burr
Assistant Examiner—Aaron J. Lewis
Attorney, Agent, or Firm—Shoemaker and Mattare, Ltd.

[57] ABSTRACT

An intermittent oxygen delivery system for supplying oxygen to a first nare of a nasal cannula in response to patient's exhalation sensed through the second nare which is isolated from the delivery of the oxygen to the first nare.

2 Claims, 1 Drawing Sheet

5,137,017

DEMAND OXYGEN SYSTEM

This is a continuation of application Ser. No. 07/337,375, filed Apr. 13, 1989, now abandoned, Mar. 15, 1991.

This invention relates to oxygen delivery systems and methods during supplemental oxygen therapy and, more particularly, to a system for controlling the flow of oxygen to a patient during supplemental oxygen therapy so as to provide oxygen only during the period of patient inhalation.

Prior devices and systems developed for the purpose of conserving oxygen during the delivery of oxygen have generally involved relatively complicated pneumatic and/or electromechanical devices. Simplification of the apparatus for providing intermittent delivery of oxygen in response to a patient's inhalation and exhalation cycles is desirable and has been sought.

It is, therefore, an object of the present invention to provide a simplified system for providing an intermittent flow of oxygen to a patient during supplemental oxygen therapy.

SUMMARY OF THE INVENTION

The present invention provides a system and a method for controlling the flow of oxygen from a source of oxygen to a patient through a nasal cannula where the flow is controlled by valve means that are operated in response to the initiation of exhalation by the patient. The nasal cannula that is an essential feature of the present invention consists of a conventionally shaped nasal cannula face piece having inlet and outlet conduits communicating respectively with two separate zones in the face piece which are separated by a gas-tight partition means in the face piece. The nasal cannula is provided with two nares or tubes that terminate adjacent the patient's nostrils as is conventional, however, each nare communicates with different zones in the face piece.

The inlet conduit or tube communicates with the valve means and the source of oxygen.

The outlet conduit communicates with sensing means capable of sensing the exhalation of the patient at a location remote from the patient and, when exhalation is sensed, the signal produced controls the closing of the valve means to interrupt the flow of oxygen. When the sensing means does not sense patient exhalation, or senses patient inhalation, the valve means remains open or is opened to provide a flow of oxygen to the patient through the inlet conduit and one nare of the face piece.

DETAILED DESCRIPTION OF THE INVENTION

Figure 1:
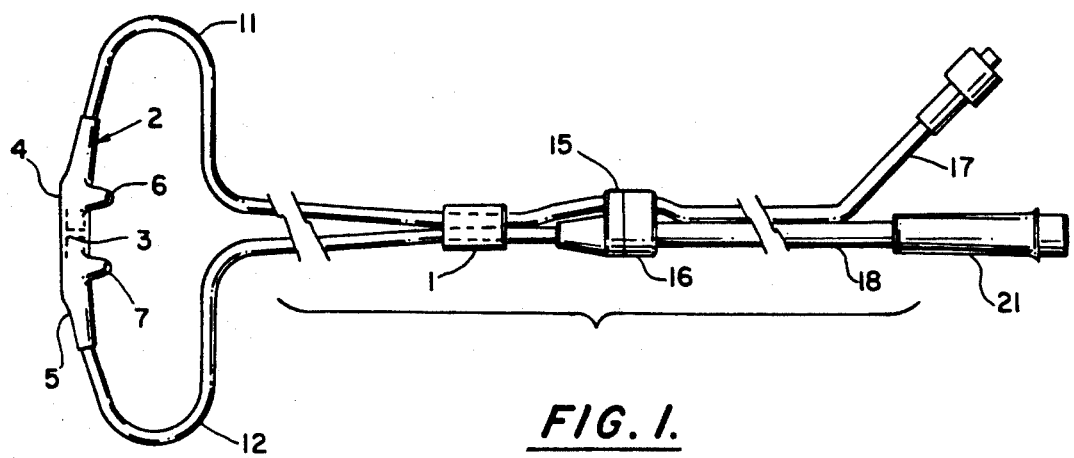
FIG. 1 is a plan view of the nasal cannula used in the present invention.
Figure 2:
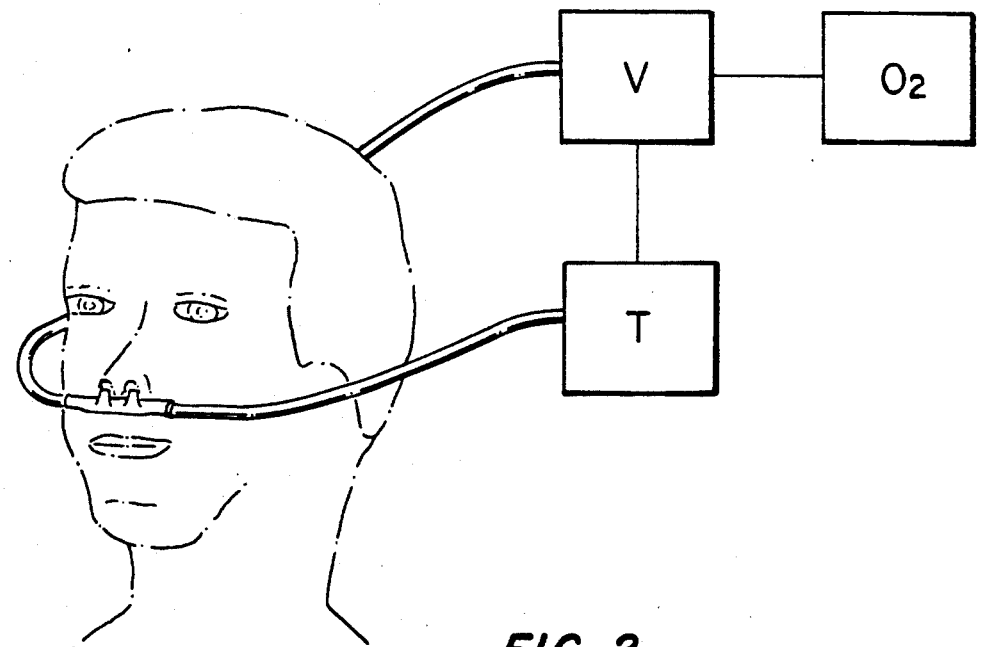
FIG. 2 is a schematic of the system for practicing the method of the present invention.

Referring to FIG. 1, a dual cannula is illustrated having a face piece 2 having a dividing web or partition 3 which divides the cannula face piece 2 into two separate zones 4 and 5 into which nares 6 and 7, respectively, communicate. In the embodiment shown, zone 4 also communicates with sensing tubing 11. Zone 5 communicates with delivery tubing 12. Tubing 11 and 12 can be the same or different outside or inside diameters. Both tubes 11 and 12 terminate in a connector 15. Preferably a bolo 1 is slidably received around the tubes 11 and 12 between the connector 15 and the face piece 2 so that adjustment can be provided for the cannula to fit snugly on the patient, minimizing the chance of movement of the nares 6 and 7 from their proper position adjacent the patient's nostrils. The tubes 17 and 18 are provided with a matching connector 16 to fit connector 15. Sense tubing 11 thereby communicates with tubing 17 which terminates in a connector 20 to be attached to pressure sensing unit T, schematically shown in FIG. 2. Likewise delivery tubing 12 communicates with tubing 18 which is connected by means of a connector 21 to the valve means V shown in FIG. 2, which is connected to a source of oxygen ($O_2$ in FIG. 2). Preferably the pressure sensing unit utilizes a transducer and associated circuitry to detect changes in pressure that will occur at the initiation of exhalation and inhalation by the patient, and to produce an electrical signal capable of actuating the valve means V to open and allow oxygen delivery when the patient is not exhaling. Any sensing unit can be employed that will perform this function.

In operation, the described system of the present invention provides a method for intermittently controlling the flow of oxygen to the patient through a nasal cannula where delivery of the oxygen is restricted to one nare. The method includes providing a source of oxygen which is connected via valve means V to the one delivery nare. The breathing of the patient is sensed at the end of a sensing conduit which communicates with the nare which is not delivering oxygen, the sensing means including signal producing means for providing a control signal to operate the valve means so that changes in the pressure of the gas in the sensing conduit, produced for example by the exhalation of the patient into the sensing nare, will produce a signal that is utilized to close the valve means and reduce or stop the delivery of oxygen from the source of oxygen to the delivery conduit and the delivery nare.

Likewise inhalation by the patient will produce a signal to open the valve means thereby supplying oxygen to the delivery nare. The foregoing method for controlling the flow of oxygen through a nasal cannula depends on the system being provided with the components and functions described and the provision of the nasal cannula described, having a gas-tight partition separating the face piece into two zones where a delivery nare communicates with one zone and a sensing nare with other zone. With the face piece properly located, the system and method of the present invention are capable of delivering sufficient oxygen to accommodate the range of flow rates normally prescribed for supplemental oxygen therapy.

It will be appreciated that choices of tubing sizes can vary from those shown or suggested and the design of the face piece and nares can deviate from those shown while still providing the gas-tight separation of the face piece into two separate zones. Likewise, the tubing shown from the connector 15, 16 to the connectors 20 and 21 can be separate tubes or multi-channel tubing.

The present invention has been described with respect to its preferred embodiment, the scope of the invention is to be limited only to the scope of the appended claims interpreted in view of the pertinent prior art.

I claim:

1. A method of conserving oxygen supplied to a patient via a nasal catheter, comprising steps of providing the catheter with two nares, one for each nostril of the patient, physically isolating the two nares from each other so that there is no fluid communication between them, feeding oxygen from a source of oxygen through only a first tube connected to only one nare of the catheter, exhausting exhaled gases from said patient through only a second tube connected only to the other nare of the catheter, sensing the onset of exhalation with a transducer connected only to said second tube, suspending flow of oxygen through said first tube by closing a valve therein responsive to said transducer when the onset of exhalation is detected, and reestablishing oxygen flow through said first tube by opening said valve when the onset of inhalation is sensed by the transducer.

2. A method of conserving oxygen supplied to a patient via a nasal catheter, comprising steps of providing the catheter with two nares, one for each nostril of the patient, physically isolating the two nares from each other so that there is no fluid communication between them, feeding oxygen from a source of oxygen through only a first tube connected to only one nare of the catheter, exhausting exhaled gases from said patient through only a second tube connected only to the other nare of the catheter, sensing the onset of exhalation with a transducer connected only to said second tube, suspending flow of oxygen through said first tube by closing a valve therein responsive to said transducer when the onset of exhalation is detected, and reestablishing oxygen flow through said first tube by opening said valve when exhalation is no longer sensed by the transducer.

* * * * *